United States Patent [19]

Wurster et al.

[11] Patent Number: 5,602,245

[45] Date of Patent: Feb. 11, 1997

[54] ONE VESSEL STEREOSELECTIVE GLYCOSYLATION OF PURINES AND PYRIMIDINES

[75] Inventors: Julie Wurster, Atlanta; Dennis C. Liotta, McDonough; Jianying Wang, Atlanta, all of Ga.; Lawrence J. Wilson, Palo Alto, Calif.

[73] Assignee: Emory University, Atlanta, Ga.

[21] Appl. No.: 970,691

[22] Filed: Nov. 4, 1992

[51] Int. Cl.$^6$ ............................ C07H 1/00; C07H 19/00; C07C 313/14; C07D 305/10
[52] U.S. Cl. ........................... 536/55.3; 549/479; 568/65
[58] Field of Search ................................ 536/27.21, 28.4, 536/55.3, 26.71, 27.6, 27.81, 28.1; 549/479; 568/65

[56] References Cited

U.S. PATENT DOCUMENTS 5,175,267  12/1992  Chu ............................................ 536/24

OTHER PUBLICATIONS

Kawakami et al. Chem. Lett. 1459–1462, 1990.
Wurster et al. Tetrahedron Lett. 33(39): 5689–5692, 1992.
Kim et al. Tetrahedron Lett. 33(39): 5733–5736, 1992.
Wilson et al. Tetrahedron Lett. 31(13): 1815–1818, 1990.
Chu et al. J. Ore. Chem. 55: 1418–1420, 1990.
Chu et al. Tetrahedron Lett. 29(42): 5349–5352, 1988.
Ryan et al. J. Org. Chem. 36(18): 2646–2657, 1971.
Abdel–Megied, A. E. S., et al., *Synthesis*, pp. 313(1991).
Agyei–Ave. K., and Baker, D. C., Carb. Res., vol. 53, pp. 4780(1988).
Beach, J. W., et al., *J. Org. Chem., vol. 57, pp. 2217 (1992)*.
Chow, K. and Danishefsky, S., *J. Org. Chem.*, vol. 55, pp. 4211 (1990).
Chou, T. S., et al., *Synthesis*, pp. 565 (1992).
Chu, C. K., et al., *Nucleotides, Nucleotides*, vol. 8, pp. 903 (1989).
Chu, C. K., et al., *J. Org. Chem.*, vol. 56, pp. 6503 (1991).
Chu, C. K., et al., *Tet. Lett., vol. 32, pp. 3791 (1991)*.
Chu, C. K., et al., *J. Org Chem.*, vol. 55, pp. 1418 (1990).
De Clerg. E., Adv. Drug Res. vol. 17, pp. 1 (1988).
DeClerg, E., J. Antimier, Chemother. Suppl. A, vol. 23, pp. 35 (1989).
Dueholm, K. L., and Pederson, E. B., Synthesis, pp. 1 (1992).
El–Laghdach, A., et al., "Selenium–controlled Stereoselective Synthesis of 2'–Deoxynucleosides from Glycals, A. Formal Synthesis of AZT," *Tetrahedron Lett.*, 34:17 2821–2822 (1993).
Hager, M. W., and Liotta, D. C., *J.A.C.S.*, vol. 113, pp. 5117 (1991).

Howell, H. G., et al., *J. Org. Chem., 53, 85 (1988)*.
Jung, M. E. and Gardiner, J. M., *Tetrahedron Lett.*, 33, 3841 (1992).
Kahne, D., et al., J.A.C.S., vol. 111, pp. 6881 (1989).
Kawakami, H., et al., "Nucleoside Synthesis from Furanoid Glycals," Heterocycles, 36:4 665–669 (1993).
Motawia, M. S. and Pederson, E. B., *Liebigs. Ann. Chem.*, pp. 1137, 1990.
Mukai, T., et al., Chem. Lett., pp. 1809 (1985).
Nicolaou, K. C., et al., J.A.C.S., vol. 105, pp.2430 (1983).
Nicolaou, K. C., et al., J.A.C.S., vol. 109, pp. 2822 (1987).
Niedballa, U. and Vorbruggern, H., J. Org. Chem., vol. 39, pp. 3660 (1974).
Norbeck, D. W., et al., *Tetrahedron Lett.*, vol. 30, pp. 6263 (1989).
Okabe, M., et al., *J. Org. Chem.*, vol. 53, pp. 4780 (1988).
Okabe, M., et al., *J. Org. Chem.*, vol. 56, pp. 4392 (1991).
Okauchi, T., et al., Chem. Lett., pp. 801 (1989).
Paulsen, H. and Tietz, H., Angew. Chem. Int. Engl., vol. 24, pp. 128 (1985).
Pozsgay, V., Jenningsm H. J., J. Org. Chem., vol. 52, pp. 4335, (1987).
Ratcliffe, A. J., et al., J.A.C.S., vol. 112, pp. 5665 (1990).
Robins, M. J., et al., Tet. Lett., vol. 25, pp. 367 (1984).
Sugimura, H., et al., *Tet. Lett.*, vol. 32, pp. 1809 (1991).
Vorbruggen, H., et al., Chem. Ber., vol. 114, pp. 1234, 1256, 1279 (1981).
Wang, J., et al., "Stereocontrolled Glycosylations via Additions of Sulfur Electrophiles to Glycals," Tetrahedron Lett. 34:31 4881–4884 (1993).
Watanabe, et al., Nucleosides, Nucleotides, vol. 1, pp. 1 (1974).
Wilson, L. J., et al., "Diastereoselective Sulfenvlation Reactions Employing N–(Phenylthio)lactams under Nonbasic Condition," *J. Org. Chem.* 57, 1948–1950 (1992).

*Primary Examiner*—Gary L. Kunz
*Attorney, Agent, or Firm*—Cheryl K. Zalesky; Kilpatrick & Cody

[57] ABSTRACT

A process for the preparation of 2',3' dideoxynucleosides, 2'-deoxynucleosides, and 2',3'-dideoxy-2',3'-didehydro-nucleosides is provided that includes the synchronous addition of a stereoselecting moiety (a directing group) and a protected purine or pyrimidine base to 5-(S)-6-(protected-oxy)-4,5-dihydrofuran in the presence of a Lewis acid. This one vessel reaction eliminates the need to separately prepare and purify a 2'-substituted ribose derivative that in a second step is condensed with a purine or pyrimidine base. The process can be easily modified to increase the stereoselectivity of formation of the β-anomeric nucleoside as necessary.

11 Claims, 3 Drawing Sheets

ONE VESSEL STEREOSELECTIVE GLYCOSYLATION OF PURINES AND PYRIMIDINES

The government has rights in this invention by virtue of NIH grant number NIH AI28731(5-21936) that partially funded research leading to this invention.

This application is in the area of organic synthesis, and in particular discloses a stereoselective glycosylation of purines and pyrimidines by synchronous reaction of the bases with 5- (S)-6-(protected-oxy)-4,5dihydrofuran in the presence of a Lewis acid and an aryl sulfenyl moiety to form synthetic nucleosides.

BACKGROUND OF THE INVENTION

In 1985, it was reported that the synthetic nucleoside 3'-azido-3'-deoxythymidine (AZT) inhibits the replication of human immunodeficiency virus type 1 (referred to as HIV), the etiological cause of acquired immune deficiency syndrome (AIDS). Since then, it has been demonstrated that a number of other 2',3'-dideoxynucleosides, including ddC (2',3'-dideoxycytidine), ddI (2',3'-dideoxyinosine), 3'-fluoro-3'-deoxythymidine (FLT), and 2',3'-dideoxy-2',3'-didehydrothymidine (D4T) are active against HIV. It appears that, after cellular phosphorylation to the 5'-triphosphate by cellular kinases, the 2',3'-dideoxynucleosides exhibit activity by competitive inhibition of reverse transcriptase or by chain termination of a growing strand of viral DNA.

2',3'-Dideoxynucleosides have historically been prepared by either of two routes; deoxygenation and derivatization of an intact nucleoside, or condensation of a derivatized sugar moiety with a nitrogenous base (referred to below as the "convergent" method).

The condensation of a derivatized sugar moiety with a nitrogenous base is a more versatile approach to the preparation of 2',3'-dideoxynucleosides than derivatization of an intact nucleoside, in that it offers the opportunity to easily modify both the base and the sugar portions of the molecule. This facilitates structure activity evaluations of a range of potential anti-viral candidates. Further, it does not require an intact nucleoside as a starting material, which is often expensive and can be difficult to obtain in adequate quantities.

There are several difficulties encountered in the process of condensing a derivatized sugar moiety with a nitrogenous base. One problem is the direction of the stereochemistry of the glycosylation reaction. The β-anomeric nucleoside is typically more biologically active than the corresponding α-anomeric nucleoside, and must be isolated from the mixture through an often difficult chromatographic separation.

A second problem encountered in the condensation reaction is that, since both purines and pyrimidines have more than one nitrogen in the ring, the condensation (glycosylation) reaction can occur at more than one site. It is typically desired that the $N^1$ atom in pyrimidines and the $N^9$ atom in purines become glycosylated to form the synthetic nucleoside. Under certain conditions, however, $N^3$ glycosylated pyrimidines and $N^7$ glycosylated purines are produced as side products. This lowers yield and necessitates additional purification efforts.

Many coupling reactions of purine or pyrimidine bases with ribose type carbohydrates employ the silyl variant of the Hilbert-Johnson procedure developed by Vorbruggen. Vorbruggen, H.; Kroilkiewicz, K.; Bennua, B. Chem. Ber. 1981, 114, 1234. This process involves the condensation of an oxygen and/or nitrogen trimethylsilylated pyrimidine or purine base with a ribose using trimethylsilyl trifluoromethanesulfonate (TMSOTf) as the Lewis acid.

2'-Deoxyribose has been coupled to purine and pyrimidine bases using the Vorbruggen method. However, little or no facial selectivity is observed in the glycosylation reaction due to the absence of the 2'-hydroxyl group in the ribose, that would otherwise direct the addition of the base to the β-face of the sugar through a neighboring group effect. Chu, C. K.; Beach, W. J.; Ullas, G. V.; Kosugi, Y. Tetrahedron Lett. 1988, 29, 5349. The Vorbruggen glycosylation method has also been used with pyranosides (Vorbruggen, H.; Kroilkiewicz, K.; Bennua, B. Chem. Ber. 1981, 114, 1234), also without facial selectivity.

Two modest exceptions to this trend have been observed. Glycosylation of silylated thymine with a 3-fluoro-2,3-dideoxyribofuranoside results in a 5:1 stereoselectivity of the β-anomer. Agyei-Aye, K.; Baker, D.C. Carb. Res. 1988, 53, 4780. Glycosylation of silylated thymine with the 3-O-ethyl-methyl sulfoxide ribofuranoside results in an 8:1 stereoselectivity of the β-anomer. Okauchi, T.; Kubota, H.; Narasaka, K. Chem. Lett. 1989, 801.

Another problem in the preparation of 2'-deoxyribose nucleosides, identified by Vorbruggen (Vorbrugen, H.; Kroilkiewicz, K.; Bennua, B. Chem. Ber. 1981, 114, 1234), is that α- and β-anomers equilibrate under the Vorbruggen reaction conditions, and therefore, enantiomeric excesses of the β-anomer that are produced can be lost.

To overcome the lack of stereoselectivity in the glycosylation of 2'-deoxyribose derivatives with purine and pyrimidine bases, 2-substituted ribosides have been used in place of 2-deoxyribose, with the hope that the 2-substituent can control the selectivity of the glycosylation reaction. In early work in this area, Ryan, K. J., et al., J. Org. Chem. 1971, 36, 2646, reported that 2-benzylthioribose can be reacted with 6-chloropurine to provide a ratio of β to α anomer of 2'α-thiobenzyl-2'-deoxy purine nucleoside of 2:1, in 38% yield.

Chu, et al., have reported that 2-α-phenylselenenyl ribose can be coupled with silylated thymine to provide a mixture of β- and αanomers of the corresponding nucleoside in a 99:1 ratio. Chu, C. K.; Babu J. R.; Beach, J. W.; Ahn, S. K.; Huang, H.; Jeong, L. S.; Lee, S. J. J. Org. Chem. 1990, 55, 1418. In this reaction scheme, 5-O-protected-3,4-(dihydro)-3-(α and β)-(aromatic or aliphaic)-selenenyl-(2(5H)-furanone is converted to 1-O-activated-2-(aromatic or aliphatic)-selenenyl-5-O-protected ribose which is reacted with a protected heterocyclic base in the presence of trimethylsilyl triflate or a Lewis acid to form a β-anomeric nucleoside. While this reaction scheme provided very high β-stereoselectivity, the process still required a two step procedure in which the 2-substituted ribose is prepared and purified and then reacted with the silylated base.

It has also been reported that a 2α-phenylthio moiety in a ribose will control the stereochemistry of the glycosylation reaction. Wilson, L. J.; Liotta, D. Tetrahedron Lett. 1990, 31, 1815. Kawakami, H.; Ebata, T.; Koseki, K.; Matsushita, H.; Naoi, Y.; Itoh, K. Chem. Lett. 1990, 1459. As shown in Scheme 1 below, for example, it was found that 2α-phenylthio-2',3'-dideoxyribofuranoside and silylated thymine can be condensed in the presence of stannic chloride to provide the desired β-anomer of the nucleoside in good yield. The phenylsulfenyl group is then removed via oxidative elimination to give D4T (2',3'-dideoxydidehydrothymidine). In similar fashion, silylated N⁴-acetyl-cytosine and uracil are coupled with high stereoselectivity.

The 2-substituted ribose used in this reaction is prepared from a protected-4-hydroxymethyl-2-phenylsulfenyl butyrolactone, which is initially formed as a mixture of isomers (2-1:1, trans:cis) through formation of the enolate. The production of a mixture of isomers lowered yield and necessitated purification steps. It was later discovered that the desired trans protected-4-hydroxymethyl-2-phenylsulfenyl butyrolactone can be formed in much larger selectivity (9–22:1) and better yields by using the silyl ketene acetal and N-phenylthio-amides. This improved the overall stereoselectivity of the process, however, the process still required a two step procedure in which the 2-substituted ribose is prepared and purified and then reacted with the silylated base. Further, this procedure cannot be used for the preparation of purine nucleosides because a mixture of $N^7$ and $N^9$ glycosylated purine isomers are obtained.

Kim, et al., have recently reported that 2',3'-dideoxy and 2',3'-dideoxy-2',3'-didehydronucleosides can be prepared with high β-stereoselectivity by condensing a furanoid glycal (5-(S)-6-(protected-oxy)-4,5-dihydrofuran) with a purine or pyrimidine base in the presence of Niodosuccinimide. Kim, et al., *Tetrahedron Letters*, Vol 33(39), 5733–5736 (1992).

Given the pharmaceutical importance of 2',3'-dideoxynucleosides, 2'-deoxynucleosides, and 2',3'-dideoxy-2',3'-didehydronucleosides, it would be of significant benefit to have a facile process for their production in which the base is glycosylated with high β-stereoselectivity without the formation of undesired $N^7$ glycosylated purines or $N^3$ glycosylated pyrimidines. It would also be of benefit to have a process for the preparation of 2',3'-dideoxynucleosides and 2',3'-dideoxy-2',3'-didehydronucleosides that can be easily modified to increase the stereoselectivity of formation of the β-anomer as necessary.

It is therefore an object of the present invention to provide a process for the preparation of 2',3'dideoxynucleosides 2'-deoxynucleosides, and 2',3'-dideoxy-2',3'-didehydronucleosides in which a purine or pyrimidine base is glycosylated to form a β-anomeric nucleoside with high stereoselectivity.

It is another object of the present invention to provide a process for the preparation of 2',3'-dideoxynucleosides, 2'-deoxynucleosides, and 2',3'-dideoxy-2',3'-didehydronucleosides in which a stereoselecting moiety can be positioned in the ribose to direct glycosylation without the need for a separate isolation and purification step.

It is a further object of the present invention to provide a process for the preparation of 2'-deoxy purine nucleosides that results in a high yield of the $N^9$-glycosylated isomer.

It is another object of the present invention to provide a process for the preparation of 2',3'-dideoxynucleosides, 2'-deoxynucleosides and 2',3'-dideoxy-2',3'-didehydronucleosides that can be easily modified to increase the stereoselectivity of formation of the β-anomer as necessary.

SUMMARY OF THE INVENTION

A process for the preparation of 2',3'dideoxynucleosides, 2'-deoxynucleosides, and 2',3'-dideoxy-2',3'-didehydronucleosides is provided that includes the synchronous addition of a stereoselecting moiety (a directing group) and a protected purine or pyrimidine base to 5-(S)-6-(protected-oxy)-4,5-dihydrofuran in the presence of a Lewis acid. This one vessel reaction eliminates the need to separately prepare and purify a 2'-substituted ribose derivative that in a second step is condensed with a purine or pyrimidine base. The process can be easily modified to increase the stereoselectivity of formation of the β-anomeric nucleoside as necessary.

The stereoselecting moiety is an aryl sulfenyl compound of the structure:

wherein Z is any appropriate leaving group under the conditions of reaction, including but not limited to halo, —O—C(O)(alkyl or aryl), —NH—C(O)(alkyl or aryl), or —SO₂(alkyl or aryl), X is alkyl, aryl, nitro, halo, or CN, and N is 0, 1, 2, 3, 4, or 5.

The aryl sulfenyl moiety must be sufficiently electrophilic that it reacts efficiently with the 5-(S)-(protected oxy) -2,3-dihydrofuran under the conditions of use. Examples of suitable stereodirecting moieties include 2,4,6-triiospropylphenylsulfenyl chloride, phenylsulfenyl chloride, 2-nitrophenylsulfenyl chloride, and 4-nitrophenylsulfenyl chloride.

The initial product of the reaction of 5-(S)-6-4,5-dihydrofuran with the protected base in the presence of a Lewis acid and an aryl sulfenyl compound is a 5'-O-protected-2'-α-(aryl sulfenyl)-3'-deoxy-β-(purine or pyrimidine)nucleoside. This compound can be converted to a 2',3'-dideoxynucleoside by nucleophilic displacement of the aryl sulfenyl moiety with a nucleophile other than hydroxy, methoxy or carboxylate as known to those skilled in the art, including by treatment with trialkyl tin hydride. The 5-O-protected-2'-α-(aryl sulfenyl-3'-deoxy-β-(purine or pyrimidine) can be converted to a 2',3'-dideoxy-2',3'-didehydronucleoside by oxidation of the sulfide to the sulfoxide, and pyrolysis of the resulting sulfoxide as known to those skilled in the art, including by treatment with a peroxy acid followed by heat. A 2'-deoxynucleoside can be prepared by reaction of a 4-substituted-5-(S)-(protected-oxy)-2,3-dihydrofuran, wherein the substituent is $N_3$, OH, halo, alkyl, aryl, $NH_2$, or O-alkyl

DETAILED DESCRIPTION OF THE INVENTION

The term alkyl, as used herein, unless otherwise specified, refers to a saturated straight, branched, or cyclic hydrocarbon of $C_1$ to $C_{15}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term alkoxy, as used herein, and unless otherwise specified, refers to a moiety of the structure -O-alkyl.

The term halo, as used herein, includes fluoro, chloro, bromo, and iodo.

The term "suitable leaving group" means a functional group that is cleaved from the parent molecule under the conditions of use. In the case of the aryl sulfenyl stereodirecting compounds defined above, Z is the leaving group.

The term protected-oxy refers to an oxygen atom that has been protected from undesired reactions with any of the oxygen protecting group known to those skilled in the art, including but not limited to, for example, a trisubstituted silyl group such as trimethylsilyl, dimethylhexylsilyl, t-butyldimethylsilyl, t-butyldiphenylsilyl, trityl, alkyl group, acyl groups such as acetyl, propionyl, benzoyl, p-$NO_2$ benzoyl, or toluyl, methylsulfonyl, or p-toluenesulfonyl.

A protected purine or pyrimidine base refers to a purine or pyrimidine in which nitrogen or oxygen groups on the base are protected from undesired reactions. Protecting groups are well known to those skilled in the art, and include but are not limited to trimethylsilyl, dimethylhexylsilyl, t-butyldimethylsilyl, and t-butyldiphenylsilyl, tritylmethyl, alkyl groups, acyl groups such as acetyl and propionyl, methylsulfonyl, and p-toluenesulfonyl.

A one vessel stereoselective glycosylation of purines and pyrimidines is disclosed in which the base is glycosylated with high β-stereoselectivity without the formation of undesired $N^7$ glycosylated purines or $N^3$ glycosylated pyrimidines. The process includes the synchronous addition of a stereoselecting moiety (a directing group) and a protected purine or pyrimidine base to 5-(S)-6-(protected-oxy)-4,5-dihydrofuran in the presence of a Lewis acid. The one vessel reaction is carried out in two parts, sulfenylation of the 5-(S)-(protected-oxy)-2,3-dihydrofuran, followed by glycosylation of the sulfenylated product with a silylated purine or pyrimidine base. This reaction eliminates the need to separately prepare and purify a 2'-substituted ribose derivative that in a second step is condensed with a purine or pyrimidine base. Importantly, the process can be easily modified to increase the stereoselectivity of formation of the β-anomer as necessary, by simply modifying the electrophilic character or bulk of the directing group.

The key starting material, 5-(S)-6-(protected-oxy)-4,5-dihydrofuran (referred to below as a "glycal" or "furanoid glycal"), can be prepared as shown in Scheme II below, or as described in Kim, et al., *Tetrahedron Letters*, Vol 33(39), 5733–5736 (1992). Mild reduction of 1 with DIBAL-H yielded lactol 1A quantitatively, which was treated without purification with thionyl chloride and triethylamine. After purification, glycal 2 necessitated storage in an inert atmosphere and in the absence of light, as it polymerizes readily under both hydrolytic and photolytic conditions.

Figure 1:
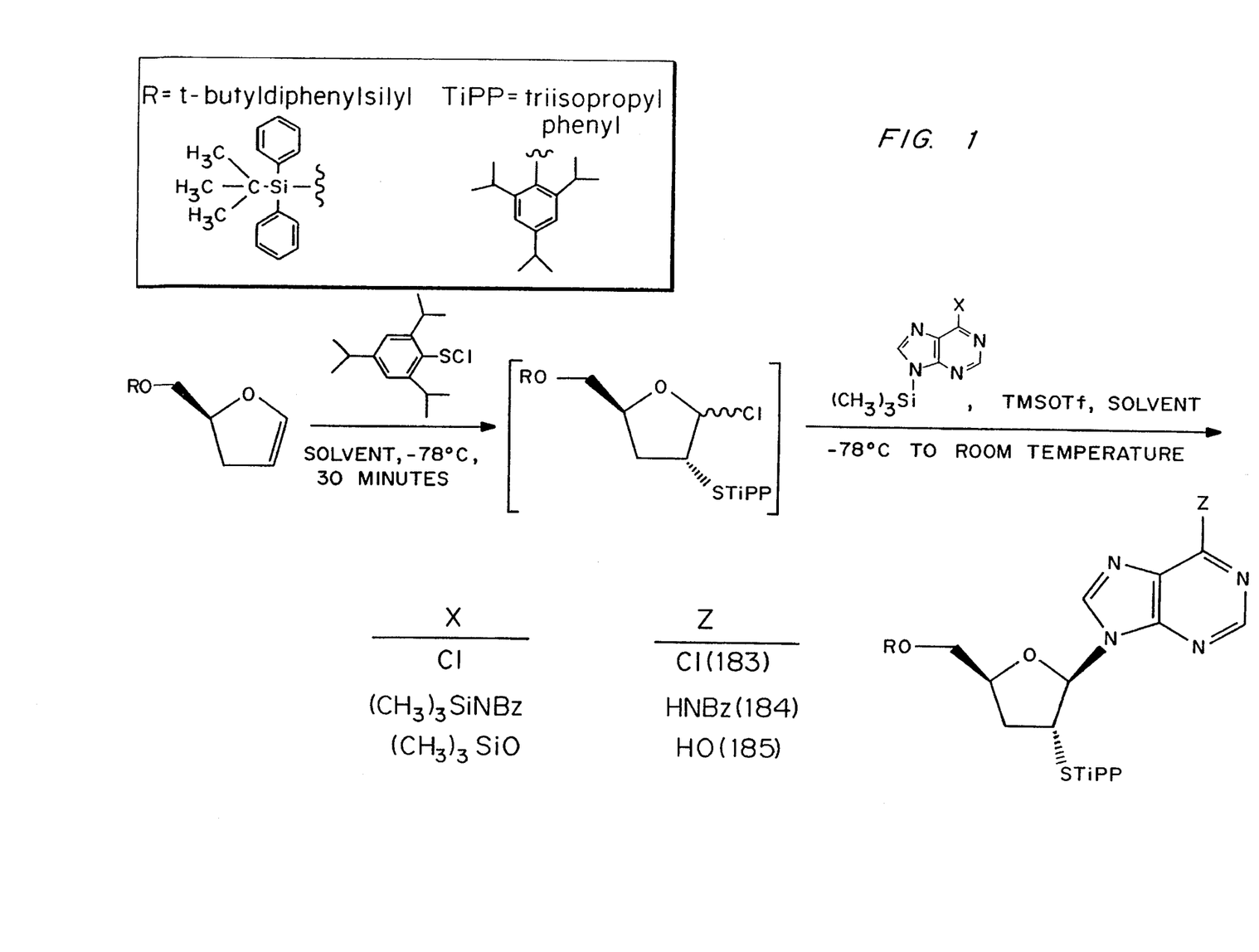
FIG. 1 is an illustration of the general reaction scheme for the synchronous addition of aryl sulfenyl chlorides and silylated purine to a 5-(S)-6-(protected-oxy)4,5-dihydrofuran.
Figure 2:
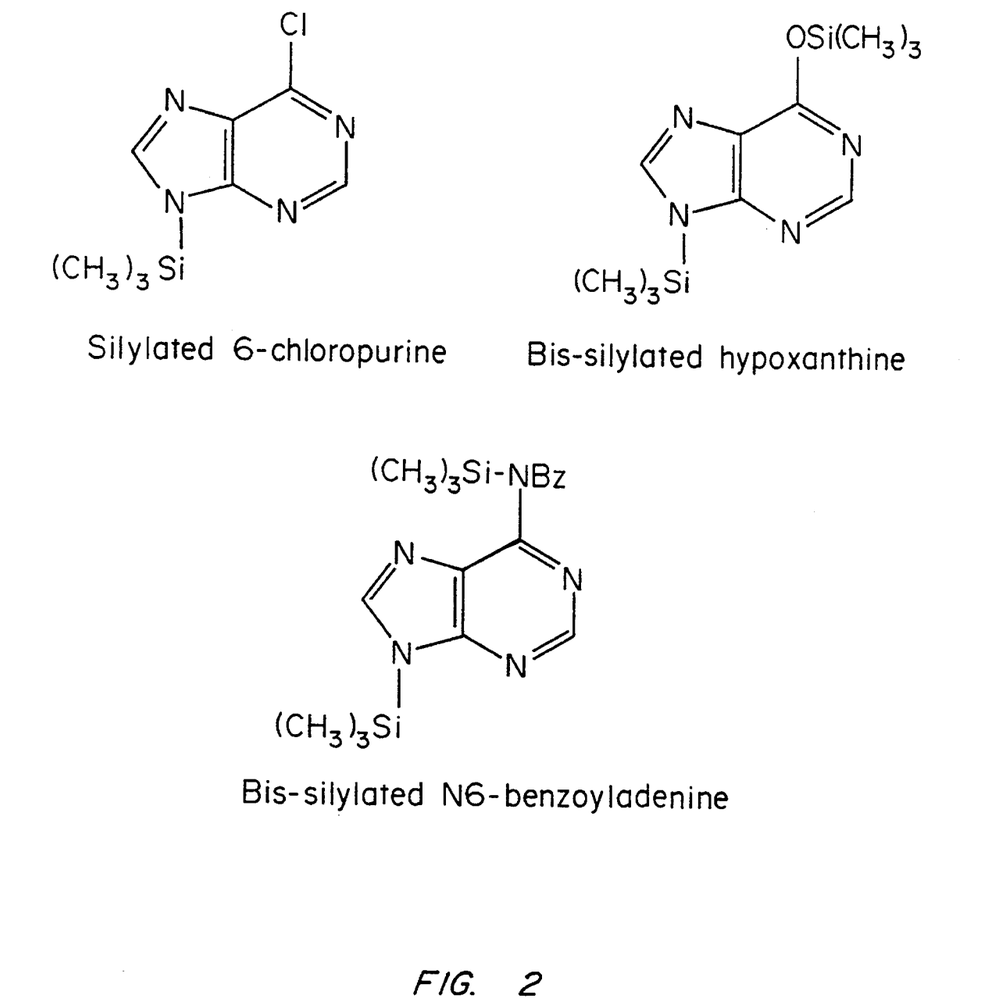
FIG. 2 is an illustration of the chemical structures of silylated 6-chloropurine, bis-silylated hypoxanthine, and bis-silylated $N^6$-benzoyladenine.
Figure 3:
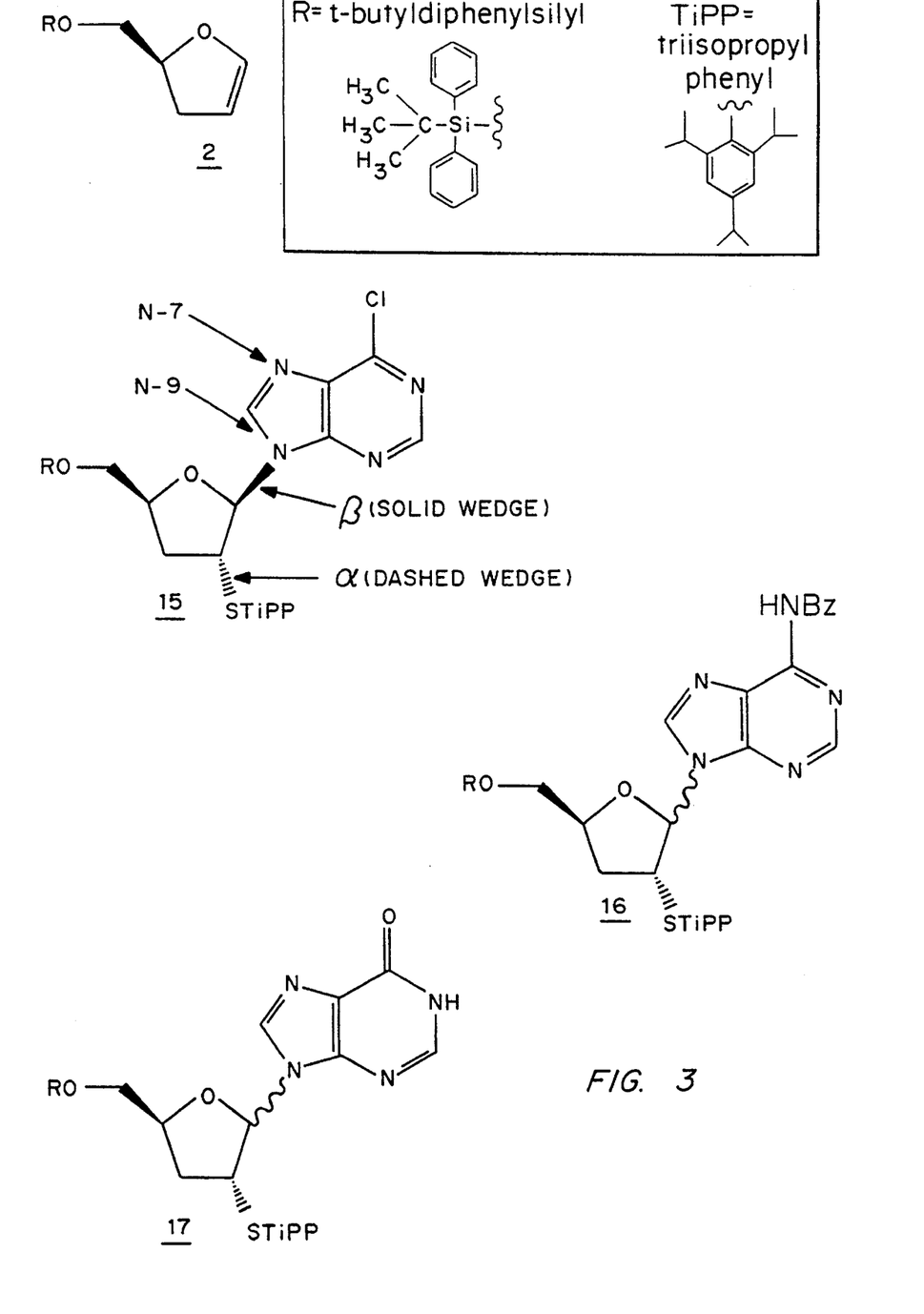
FIG. 3 is an illustration of the chemical structures of 5-(S)-6-(t-butyldiphenylsilyloxy)-4,5-dihydrofuran (compound 2), and Compounds 15, 16 and 17.

The glycal 2 is added to the aryl sulfenyl stereodirecting compound in an organic solvent at a low temperature such that undesired side reactions do not occur, as illustrated in FIG. 1. Any organic solvent can be used that does not adversely affect the reaction. In general, the least polar solvent that can dissolve the reactants is used. Diethyl ether is a solvent of choice. When the reactants are not soluble in diethyl ether, other solvents such as chlorinated hydrocarbons including methylene chloride, toluene, acetonitrile, tetrahydrofuran, and mixtures thereof may be appropriate.

The reaction is typically performed at a nonlimiting temperature range of between approximately −78° C. (temperature of dry ice in acetone) and 60° C., preferably between −78° and 25° C., usually between −40° C. and 0° C. The optimal temperature will vary depending on the base and stereodirecting moiety employed, and can be easily determined.

The reaction is typically carried out in an inert atmosphere such as nitrogen or argon, however, adequate yields may be obtained under certain situations without inert gas cover. The solution and the reagents should be very dry to obtain an appreciable yield.

The reaction is typically finished in 30 minutes to several hours, and can be monitored, if desired, by thin layer chromatography. The starting glycal polymerizes to a small extent when applied to silica gel.

The sulfenylated intermediate is then coupled with a silylated pyrimidine or purine nucleoside base in the presence of a Lewis acid by adding the reagents to the intermediate in solution.

The choice of both solvent and Lewis acid are important to the stereochemical outcome of this second stage of the reaction, and differ for pyrimidines and purines. The Lewis acid $SnCl_4$ chelates with the sulfenyl moiety attached to the 2-position of the 2-deoxyribosylfuranoside. This chelation sterically blocks the α-face of the 2-deoxyribosylfuranoside, thereby directing glycosylation to the desired β-face. In the case of pyrimidine nucleoside bases, therefore, the preferred Lewis acid is $SnCl_4$. It has also been discovered that while any inert organic solvent can be used for the glycosylation reaction, the solvent that provides the highest degree of B-stereoselectivity in the preparation of pyrimidine nucleosides is $CH_2Cl_2$.

In contrast, it is known that an unfavorable mixture of $N^9$ and $N^7$ glycosylated purine nucleosides are produced when $SnCl_4$ is used as the Lewis acid. It is also known that when TMSOTf is used as the Lewis acid, the undesired $N^7$ isomer is not produced. It was predicted, therefore, in this reaction that TMSOTf would eliminate the undesired production of $N^7$ isomers at the expense of a loss of facial bias, and cause the production of unwanted mixtures of β- and α-anomeric nucleosides. It was discovered, however, that contrary to expectations, reactions of 6-chloropurine, hypoxanthine and $N^6$-benzoyladenine with sulfenylated intermediate provide predominantly one isomer, the trans-β-$N^9$ isomer. Apparently, non-sulfur chelating Lewis acids such as TMSOTf direct glycosylation based on the steric effect of the size of both the aryl sulfenyl moiety and the purine or pyrimidine base. The purine condensation reaction is more solvent dependent than the pyrimidine condensation. Diethyl ether was often the solvent of choice in the more non-polar purines (6-chloropurine and hypoxanthine), whereas, methylene chloride allowed for greater stereoselection in the case of the more polar $N^6$-benzoyladenine.

I. Preparation of 2-(S)-(t-butyldiphenysilyloxymethyl)-3,4-dihydrofuran (compound 2)

To 3.55 g (10 mmol) of (S)-lactone (1) dissolved in 46 mL of toluene at –78° C. was added 11.5 mL (11.5 mmol) of a diisobutylaluminum hydride/hexanes solution (1M, Aldrich), dropwise, over a 25 minute period. The mixture was stirred for 3 hours at –78° C., and then quenched with 10 mL of saturated $NH_4Cl$ solution. After warming to room temperature, the mixture was extracted with ether, followed by washing with $H_2O$, $NaHCO_3$ (twice), and NaCl solutions. The aqueous layers were re-extracted with ether, and the organic layers were combined and dried over $MgSO_4$. Filtration and solvent removal in vacuo gave a colorless, slightly cloudy oil. This oil was then dissolved in 46 mL of $CH_2Cl_2$ and cooled to 0° C. Next, 1.1 mL (15.1 mmol) of $SOCl_2$ was added, and the solution stirred for 10 minutes at 0° C. Then, 7 mL (50.2 mmol) of $NEt_3$ was carefully added over a 10 minute period. The mixture was then warmed to room temperature and stirred for 36 hours. The resulting dark brown mixture was then taken up in $CH_2Cl_2$, and then washed with $H_2O$, $NaHCO_3$ (twice), and NaCl solutions. The aqueous layers were re-extracted with $CH_2Cl_2$, and the organic layers were combined and dried over $MgSO_4$. Filtration followed by solvent removal in vacuo gave a black, viscous oil. Filtration over a 2 inch plug of silica with 8:1-Hexanes:EtOAc, followed by solvent removal gave an orange oil. Column chromatography (9:1-Hexanes:EtOAc, 1% $NEt_3$) gave 2.19 g (65%) of a yellow oil. The material obtained was diluted with hexanes and the resulting solution mixed with Norit decolorizing carbon. The mixture was filtered and solvent removed to give 2.12 g (63%) of a clear oil (which gradually became a pink color). An analytically pure sample was prepared by additional column chromatography.

Physical data for 2: $^1$NMR (300 MHz, $CDCl_3$): d 1 06 (s, 9H), 2.45 (m, 1H), 2.63 (m, 1H), 367 (dd, 1H, J=4.8 Hz, J=10.8 Hz), 375 (dd, 1H, J=5.7 Hz, J=10.8 Hz), 4.66 (m, 1H), 4.84 (d, 1H, J=2.4 Hz), 6.26 (d, 1H, J=2 Hz), 7.40 (m, 6H), 7.68 (d, 4H, J=6.6 Hz); $^{13}$C NMR (75.5 MHz, $CDCl_3$): d 18.77, 26.28, 30.67, 65.36, 80.65, 98.43,127.12, 129.11, 133.04, 135.09, 144.64; IR ($CH_2Cl_2$): 3080, 2940, 1620, 1430, 1110, 1060 cm$^{-1}$; MS (FAB, H$^+$): 339 (M+H)$^+$, 281, 261 225 182 162, 125; Anal. Calc. for $C_{21}H_{26}O_2Si$: C, 74.51%, H, 7.74%; Found: C, 74.59%, H, 7.75%; Obsvd [a]$_{289}$=+33.89 (c=0.0102, $CHCl_3$).

II. Preparation of 2,4,6-Triisopropylbenzenethiol (4).

4.74 g (0.125 moles) of lithium aluminum hydride was placed in a 250 mL three necked round bottom flask equipped with a reflux condenser under an Ar(g) atmosphere, along with 50 mL of $Et_2O$, and the mixture cooled to 0° C. To this slurry was added 15.14 g (0.050 moles) of 2,4,6-triisopropyl benzenesulfonyl chloride (3, Aldrich) in 70 mL of ether via cannula while stirring over a 40 minute period. Upon completion of addition, the vessel was removed from the bath and allowed to warm to room temperature over a 2 hour period, and then refluxed for an additional 5 hours. The mixture was then cooled to 0° C., and quenched by the addition of 5 mL $H_2O$, 5 mL of 5% HCl (aq), and 15 mL $H_2O$. The quenched mixture was allowed to warm to room temperature, and 20 grams of $MgSO_4$ added. After standing for 20 minutes, the mixture was filtered over a plug of silica gel with ether to give 11.31 g (96%) of a slightly brown oil after solvent removal.

Physical data for 4: $^1$H NMR (300 MHz, $CD_2Cl_2$): d 1.22 (d, 6H, J=6.6 Hz), 1.24 (d, 12H, J=6.9 Hz), 2.85 (quin, 1H, J=6.9 Hz), 3.13 (s, 1H), 3.49 (quin, 2H, J=6.9Hz), 6.99 (s, 2H); $^{13}$C NMR (75.5 MHz, CDCl$_3$): d 23.59, 24.42, 32.12, 34.53, 121.55, 124.65, 147.30, 148.42; IR (neat): 3070, 2980, 1610, 1580, 1470, 1440, 1390, 1370 cm$^{-1}$.; MS (EI): 236 (M)+, 221, 127, 115, 91, 77, 65; HRMS (EI): For C$_{15}$H$_{24}$S:

Calc. m/e=236.4146; Obsvd. m/e=236.1608.

III. Preparation of 2,4,6-Triisopropylphenylsulfenyl chloride (5).

N-Chlorosuccinimide (1.41 g, 11 mmol, 1.1 equiv.) was dissolved in 15 mL CH$_2$Cl$_2$, and cooled to 0° C. Then 2.36 g (10 mmol) of 2,4,6-triisopropylbenzenethiol (4) was added (neat) dropwise over a 10 minute period.[72] The mixture was stirred at 0° C. for 30 minutes, and then warmed to room temperature over 45 minutes. The mixture was initially yellow and then gradually turned orange. The solvent was then removed in vacuo. Hexanes were then added to precipitate the succinamide. The solution was filtered over celite, and the hexanes were removed in vacuo to provide an orange oil, which was immediately used in the subsequent reaction.

Physical data for 5: $^1$H NMR (300 MHz, CD$_2$Cl$_2$): d 1.25 (d, 6H, J=6.9 Hz), 1.28 (d, 12 H, J=6.9 Hz), 2.92 (quin, 1H, J=6.9 Hz), 4.01 (quin, 2H, J=6.9Hz), 7.12 (s, 2H); MS (FAB, H$^+$NAB): 705 (3M-3Cl$^-$)$^+$, 470 (2M-2Cl$^-$)$^+$, 235 (M-Cl$^-$)$^+$, 191, 149.

IV. Condensation of 5-(S)-6-(protected-oxy)-4,5-Dihydrofuran with Pyrimidine Bases The examples below set out the experimental conditions and product yields for reactions of compound 2 with a variety of silylated pyrimidine bases and stereodirecting aryl sulfenyl moieties in various solvent systems, Lewis bases, and temperatures.

EXAMPLE 1

One Vessel Reaction of Compound 2 with 2,4,6-Triisopropylphenylsulfenyl chloride (TIPPSCl) and Silylated-N-acetylcytosine.

One-pot Reaction of Dihydrofuran with 2,4,6-Triisopropylphenylsulfenyl chloride (TIPPSCl) and Silylated-N-acetylcytosine

| Entry | Lewis Acid[a] | Solvent | Condition[b] | Ratio[c] (6a:6b) | Time (h) | Yield[d] (%) |
|---|---|---|---|---|---|---|
| 1 | SnCl$_4$ | CH$_2$Cl$_2$ | −78 to 0° C. to r.t. | 11:1 | 3 | 65 |
| 2 | SnCl$_4$ | Et$_2$O | −78 to 0° C. to r.t. | 11:1 | 3 | 60 |
| 3 | TMSOTf | CH$_2$Cl$_2$ | −78 to 0° C. to r.t. | 6:1 | 2 | 73 |
| 4 | TMSOTf | Et$_2$O | −78 to 0° C. to r.t. | 3:1 | 2 | 60 |
| 5 | SnCl$_4$ | CH$_2$Cl$_2$ | −78 to 0° C. to r.t. | 14:1 | 2 | 60 |
| 6 | SnCl$_4$ | CH$_2$Cl$_2$ | −78° C. to r.t. | 23:1 | 2 | 70 |

[a]Reaction with 1.15 equiv. of Lewis acid;
[b](1) −78 to 0° C. to r.t. indicates that the sulfenylation was conducted at −78° C. for 30 minutes and the silylated base and Lewis acid then introduced at 0° C., and finally, the reaction finished at room temperature; (2) −78° C. to r.t. indicates that the sulfenylation was conducted at −78° C. for 30 minutes and base and Lewis acid were then introduced at −78° C. before the reaction mixture was warmed to room temperature.
[c]Determined by $^1$H NMR of purified product.
[d]After column chromatography.

5'-O-t-Butyldiphenylsilyl-2'α-(2,4,6-triisopropyl)phenyl thio-3'-deoxy-β-N-acetylcytosine (6) (entry 6 of Table 1)

Compound 2 (0.1840 g, 0.54 mmol, 1.0 eq) was dissolved in 3 mL of dry CH$_2$Cl$_2$ and cooled to −78° C. A freshly prepared sample of 2,4,6-triisopropylphenylsulfenyl chloride (0.1842 g, 0.68 mmol, 1.25 eq) was dissolved in 2 mL of CH$_2$Cl$_2$ and then added to the solution of compound 2, and the reaction mixture stirred under N$_2$ for 30 minutes. A CH$_2$Cl$_2$ solution (1 mL) of silylated-N-acetylcytosine (0.1860 g, 0.62 mmol, 1.15 eq) was then added to the reaction mixture. After SnCl$_4$ (1.0M in CH$_2$Cl$_2$, 0.62 mL, 0.62 mmol, 1.15 eq) was added, the reaction turned red brown. The mixture was stirred for 10–20 minutes at −78° C. and then allowed to warm to room temperature for about 1 hour. The solution was poured into an aqueous NaHCO$_3$ solution (30 mL) and extracted with 3×25 mL of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography (EtOAc as eluent) to give 0.2777 g of a white foam in 70% yield, which was an inseparable mixture of 6a and 6b with a ratio of 23:1 determined from $^1$H NMR by integration of the protons at the anomeric center (d: 5.98-d, J=1.0 Hz, b; 6.16-d, J=4.2 Hz, a). m.p.: 93°–95° C.

IR (CH$_2$Cl$_2$, cm$^{-1}$): 3420, 2980, 2880, 1730, 1675, 1570, 1485, 1395. $^1$H NMR (300 MHz, CDCl$_3$): d 1.07 (s, 9H), 1.18 (t, 12H, J=6.6 Hz), 1.25 (d, 6H, J=7.2 Hz), 1.75 (m, 1H), 2.25 (s, 3H), 2.30 (m, 1H), 2.90 (quin, 1H, J=6.6 Hz), 3.59 (m, 1H), 3.76 (m, 1H), (quin, 2H, J=6.6 Hz), 4.10 (m, 1H), 4.63 (m, 1H), 5.98 (d, 1H, J=1.0 Hz), 7.01 (s, 2H), 7.19 (d, 1H0, J=7.2 Hz), 7.35–7.46 (m, 6H), 7.60–7.66 (m, 4H), 8.32 (d, 1H, J=7.5 Hz), 9.87 (br, s,1H). $^{13}$C NMR (75.1 MHz, CDCl$_3$): d 19.30, 23.92, 23.95, 24.39, 24.71, 24.93, 26.85, 26.94, 30.50, 31.60, 34. 28, 54.62, 63.99, 82.16, 91.29, 96.69, 121.99,125.66, 127.75, 127.94, 127.99, 130.11, 132.43, 132.65, 135.45, 135.58, 144.32, 150.28, 153.65, 154.84, 163.27, 171.61. Analysis for C$_{42}$H$_{55}$O$_4$N$_3$SiS Calcd.: C, 69.47; H, 7.64; N, 5.79. Found: C, 69.18; H, 7.66; N, 5.52.

EXAMPLE 2

One Vessel Reaction of Compound 2 with Phenylsulfenyl chloride and Silylated-N-acetylcytosine One-pot Reaction of Dihydrofuran with Phenylsulfenyl chloride (PhSCl) and Silylated-N-acetylcytosine

| Entry | Lewis Acid[a] | Solvent | Condition[b] | Ratio[c] (7a:7b) | Time (h) | Yield[d] (%) |
|---|---|---|---|---|---|---|
| 1 | SnCl$_4$ | CH$_2$Cl$_2$ | −78 to 0° C. to r.t. | 12:1 | 2.5 | 83 |
| 2 | SnCl$_4$ | Et$_2$O | −78 to 0° C. to r.t. | 14:1 | 1.5 | 55 |
| 3 | TMSOTf | CH$_2$Cl$_2$ | −78 to 0° C. to r.t. | 5:1 | 1.5 | 60 |
| 4 | TMSOTf | Et$_2$O | −78 to 0° C. to r.t. | 4:1 | 1.5 | 50 |
| 5 | SnCl$_4$ | CH$_2$Cl$_2$ | −78° C. to r.t. | 18:1 | 2 | 65 |

5'-O-t-Butyldiphenylsilyl-2'-α-phenylthio-3'-deoxy-β-N-acetylcytidine (7) (entry 5 of Table 2)

Compound 2 (0.1738 g, 0.51 mmol, 1.0 eq) was dissolved in 3 mL of dry CH$_2$Cl$_2$ and cooled to −78° C. A freshly prepared sample of phenylsulfenyl chloride (0.0928 g, 0.64 mmol, 1.25 eq) was dissolved in 2 mL of CH$_2$Cl$_2$ and then added to the solution of compound 2. The reaction mixture was stirred under N$_2$ for 30 minutes. A CH$_2$Cl$_2$ solution (1 mL) of silylated-N-acetylcytosine (0.1757 g, 0.59 mmol, 1.15 eq) was added to the reaction mixture. After SnCl$_4$ (1.0M in CH$_2$Cl$_2$, 0.59 mL, 0.59 mmol,1.15 eq) was added, the reaction turned red brown. The mixture was stirred for 10–20 minutes at −78° C. and then allowed to warm to room temperature for about 1 hour. The solution was poured into an aqueous NaHCO$_3$ solution (30 mL) and extracted with 3×25 mL of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography (EtOAc as eluent) to give 0.1996 g of a white foam in 65% yield, which was an inseparable mixture of 7a and 7b with a ratio of 18:1 as determined from $^1$H NMR by integration of the protons at the anomeric center. (d: 6.07-d, J=2.4 Hz, b; 6.27-d, J=4.5 Hz, a). m.p.: 72°–74° C.

IR (CH$_2$Cl$_2$, cm$^{-1}$): 3420, 3080, 2890, 1730, 1675, 1560, 1485, 1320. $^1$H NMR (300 MHz, CDCl$_3$): d 1.10 (s, 9H), 1.96 (m, 1H), 2.25 (s, 3H), 2.40 (m, 1H), 3.71 (dd, 1H, J=2.7 Hz, J=12.0 Hz, ), 3.89 (m, 1H), 4.19 (dd, 1H, J=2.1 Hz, J=12.0 Hz), 4.50 (m, 1H), 6.07 (d, 1H, J=2.4 Hz), 7.15 (d, 1H, J=7.5 Hz), 7.23 (m, 4H), 7.30–7.49 (m, 7H), 7.63 (m, 4H), 8.33 (d, 1H, J=7.5 Hz), 9.64 (br, s,1H). $^{13}$C NMR (75.1 MHz, CDCl$_3$): d 19.31, 24.90, 26.86, 26.99, 31.34, 53.29, 64.14, 81.32, 91.15, 96.80, 127.74, 127.77, 127.91, 127.98, 128.00, 129.10, 130.13, 132.36, 132.64, 132.94, 133.10, 135.42, 135.60, 144.30, 155.00, 163.16, 171.44. Analysis for C$_{33}$H$_{37}$O$_4$N$_3$ Sis Calcd.: C 66.07; H, 6.22; N, 7.00. Found: C, 65.87; H, 6.46; N, 7.11.

EXAMPLE 3

One Vessel Reaction of Compound 2 with 2-Nitrophenylsulfenyl chloride and Silylated-N-acetylcytosine One-pot Reaction of Dihydrofuran with 2-Nitrophenylsulfenyl chloride (2-O2NPhSCl) and Silylated-N-acetylcytosine of compound 2. The reaction mixture was stirred under N$_2$ for 30 minutes. After SnCl$_4$ (1.0M in CH$_2$Cl$_2$, 0.63 mL, 0.63 mmol, 1.15 eq) was added to the mixture, a CH$_2$Cl$_2$ solution (1 mL) of silylated-N-acetyl cytosine (0.1884 g, 0.63 mmol, 1.15 eq) was added to the mixture. The resulting mixture was stirred for 10–20 minutes at −78° C. and then allowed to warm to room temperature for about 1 hour. The solution was poured into an aqueous NaHCO$_3$ solution (30 mL) and extracted with 3×25 mL of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography (6:1 of EtOAc/EtOH as eluent) to give 0.2116 g of a yellow powder in 60% yield, which was an inseparable mixture of 8a and 8b with a ratio of 13:1 determined from 1H NMR by integration of the protons at the anomeric center (d: 6.10-s, b; 6.50-d, J=4.5 Hz, a). m.p.: 192–194 C. IR (CH$_2$Cl$_2$, cm$^{-1}$): 3415, 3060, 2960, 1730, 1675, 1560, 1485, 1395.

$^1$H NMR (300 MHz, CDCl$_3$): d 1.12 (s, 9H), 1.95 (dd, 1H, J=4.8 Hz, J=12.5 Hz), 2.22 (s, 3H), 2.56 (m, 1H), 3.75 (dd, 1H, J=2.1 Hz, J=12.0 Hz, ), 4.14 (d, 1H, J=6.0 Hz), 4.24 (d, 1H, J=12.3 Hz), 4.59 (m, 1H), 6.10 (s, 1H), 7.20 (d, 1H, J=7.5 Hz), 7.29–7.56 (m, 9H), 7.63 (m, 4H), 7.78 (d, 1H, J=8.1 Hz), 8.10 (d, 1H, J=8.1 Hz), 8.47 (d, 1H, J=7.8 Hz), 9.36 (s,1H). $^{13}$C NMR (75.1 MHz, CDCl$_3$): d 19.33, 24.86, 26.84, 26.88, 27.00, 30.90, 51.61, 63.53, 82.13, 91.10, 96.88, 125.82, 126.19,127.77, 127.84, 127.93, 128.01, 129.82, 130.19, 132.28, 132.52, 133.39,135.42, 135.55, 144.40, 147.72, 155.07, 163.16, 171.19.

| Entry | Lewis Acid[a] | Solvent | Condition[b] | Ratio[c] (8a:8b) | Time (h) | Yield[d] (%) |
|---|---|---|---|---|---|---|
| 1 | SnCl$_4$ | CH$_2$Cl$_2$ | −78 to 0° C. to r.t. | 11:1 | 1.5 | 87 |
| 2 | SnCl$_4$ | CH$_2$Cl$_2$ | −78 to r.t. | 13:1 | 2 | 60 |

5'-O-t-Butyldiphenylsilyl-2'-α-2-nitrophenylthio-3'-deoxy-β-N-acetylcytidine (8) (entry 2 of Table 3)

Compound 2 (0.1864 g, 0.55 mmol, 1.0 eq) was dissolved in 3 mL of dry CH$_2$Cl$_2$ and cooled to −78° C. 2-Nitrophenylsulfenyl chloride (0.1201 g, 0.63 mmol, 1.15 eq) was dissolved in 2 mL of CH$_2$Cl$_2$ and then added to the solution Analysis for C$_{33}$H$_{36}$O$_6$N$_4$Sis Calcd.: C 61.47; H, 5.63; N, 8.69. Found: C, 61.57; H, 5.67; N, 8.59.

EXAMPLE 4

One Vessel Reaction of Compound 2 with 4-Nitrophenyl chloride and Silylated-N-acetylcytosine One-pot Reaction of Dihydrofuran with 4-Nitrophenylsulfenyl chloride (4-O$_2$NPhSCl) and Silylated-N-acetylcytosine

| Entry | Lewis Acid[a] | Solvent | Condition[b] | Ratio[c] (9a:9b) | Time (h) | Yield[d] (%) |
|---|---|---|---|---|---|---|
| 1 | SnCl$_4$ | CH$_2$Cl$_2$ | −78 to 0° C. to r.t. | 10:1 | 1.5 | 81 |
| 2 | SnCl$_4$ | CH$_2$Cl$_2$ | −78° C. to r.t. | 13:1 | 2 | 68 |

5'-O-t-Butyldiphenylsilyl-2'α-4-nitrophenylthio-3'-deoxy-β-N-acetylcytidine (9) (entry 2 of Table 4)

Compound 2 (0.1870 g, 0.55 mmol, 1.0 eq) was dissolved in 3 mL of dry CH$_2$Cl$_2$ and cooled to −78° C. 4-Nitrophenylsulfenyl chloride (0.1205 g, 0.64 mmol, 1.15 eq) was dissolved in 2 mL of CH$_2$Cl$_2$ and was added to the solution of compound 2. The reaction mixture was stirred under N$_2$ for 30 minutes. After SnCl$_4$ (1.0M in CH$_2$Cl$_2$, 0.64 mL, 0.64 mmol, 1.15 eq) was added to the solution, a CH$_2$Cl$_2$ solution (1 mL) of silylated-N-acetyl cytosine (0.1890 g, 0.64 mmol, 1.15 eq) was added to the mixture. The mixture was stirred for 10–20 minutes at −78 C. and then allowed to warm to room temperature for about 1 hour. The solution was poured into an aqueous NaHCO$_3$ solution (30 mL) and extracted with 3×25 mL of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography (EtOAc as eluent) to give 0.2408 grams of a yellow powder in 68% yield, which was an inseparable mixture of 9a and 9b with a ratio of 13:1 determined from $^1$H NMR by integration of the protons at the anomeric center (d: 6.05-d, J=1.8 Hz, b; 6.34-d, J=4.2 Hz, a). m.p.: 96°–98° C.

IR (CH$_2$Cl$_2$, cm$^{-1}$): 3405, 3080, 2960, 2880, 1695, 1510, 1475, 1350. $^1$H NMR (300 MHz, CDCl$_3$): d 1.10 (s, 9H), 1.97 (m, 1H), 2.22 (s, 3H), 2.52 (m, 1H), 3.74 (dd, 1H, J=2.4 Hz, J=12.0 Hz, ) 4.12 (m, 1H), 4.22 (dd, 1H, J=2.1 Hz, J=12.0 Hz), 4.52 (m, 1H), 6.05 (d, 1H, J=1.8 Hz), 7.19 (d, 1H, J=7.5 Hz), 7.28–7.48 (m, 9H), 7.50 (d, 1H, J=8.4 Hz), 7.62 (m, 4H), 8.06 (d, 1H, J=8.7 Hz), 8.37 (d, 1H, J=7.5 Hz), 9.95 (s, 1H). $^{13}$C NMR (75.1 MHz, CDCl$_3$): d 19.34, 24.86, 26.88, 27.01, 31.16, 31.21, 51.72, 63.81, 81.77, 91.19, 97.04, 123.94, 127.88, 128.05, 129.43, 130.23, 132.26, 132.52, 135.42, 135.57, 143.79, 144.13, 146.09, 155.05, 164.17, 171.27. Analysis for C$_{33}$H$_{36}$O$_6$N$_4$SiS Calcd: C, 61.47; H, 5.63. Found: C, 61.39; H, 5.94.

EXAMPLE 5

One Vessel Reaction of Compound 2 with 2,4,6-Triisopropylphenylsulfenyl chloride (TIPPSCl) and Silylated-thymine One-pot Reaction of Dihydrofuran with 2,4,6-Triisopropylphenylsulfenyl chloride (TIPPSCl) and Silylated-thymine

| Entry | Lewis Acid[a] | Solvent | Condition[b] | Ratio[c] (10a:10b) | Time (h) | Yield[d] (%) |
|---|---|---|---|---|---|---|
| 1 | $SnCl_4$ | $CH_2Cl_2$ | −78 to 0° C. to r.t. | 25:1 | 1.5 | 55 |
| 2 | $SnCl_4$ | $CH_2Cl_2$ | −78 to r.t. | 44:1 | 2 | 60 |

5'-O-t-Butyldiphenylsilyl-2'-α-2,4,6-triisopropylphenylthio-3'-deoxy-β-thymidine (10) (entry 2 of Table 5)

Compound 2 (0.1840 g, 0.54 mmol, 1.0 eq) was dissolved in 3 mL of dry $CH_2Cl_2$ and cooled to −78° C. 2,4,6-Triisopropylphenylsulfenyl chloride (0.1842 g, 0.68 mmol, 1.25 eq) was dissolved in 2 mL of $CH_2Cl_2$ and was added to the solution of compound 2. The reaction mixture was stirred under $N_2$ for 30 minutes After $SnCl_4$ (1.0M in $CH_2Cl_2$, 0.62 mL, 0.62 mmol, 1.15 eq) was added, a $CH_2Cl_2$ solution (1 mL) of silylated-thymine (0.1691 g, 0.62 mmol, 1.15 eq) was added to the reaction mixture. The mixture was stirred for 10–20 min at −78° C. and then allowed to warm to room temperature for about 1 hour. The solution was poured into an aqueous $NaHCO_3$ solution (30 mL) and extracted with 3 ×25 mL of $CH_2Cl_2$. The combined $CH_2Cl_2$ layer was washed with 50 mL of brine solution before being dried with anhydrous $MgSO_4$. After filtration and concentration, the resulting crude product was purified by flash silica gel chromatography (1:2 of EtOAc/hexanes as eluent) to give 0.2279 g of a white powder in 60% yield, which was an inseparable mixture of 10a and 10b with a ratio of 44:1 determined from $^1H$ NMR by integration of the protons at the anomeric center. (d: 6.01-d, J=6.6 Hz, b; 6.24-d, J=4.2 Hz, a) . m.p.: 144°14 146° C.

IR ($CH_2Cl_2$, $cm^{-1}$): 3400, 3052, 2980, 2880, 1693, 1470, 1270, 1120. $^1H$ NMR (300 MHz, $CDCl_3$): d 0.96 (s, 9H), 1.17 (t, 12H, J=7.2 Hz), 1.23 (t, 6H, J=7.0 Hz), 1.57 (s, 3H), 2.15 (m, 1H), 2.47 (m, 1H), 2.87 (quin, 1H, J=6.8 Hz), 3.40 (quartet, 1H, J=7 Hz, 3.65 (dd, 1H, J=2.9 Hz, J=11.6 Hz), 3.77 (quartet, 2H, J=6.8 Hz), 3.97 (dd, 1H, J=2.6 Hz, J=11.6 Hz), 4.38 (m, 1H), 6.01 (d, 1H, J=6.6 Hz), 7.01 (s, 2H), 7.20 (s, 1H), 7.34 (m, 6H), 7.60 (m, 4H), 8.51 (br, s, 1H).

$^{13}C$ NMR (75.1 MHz, $CDCl_3$): d 12.18, 19.30, 23.96, 24.02, 24.32, 24.52, 26.96, 31.75, 33.99, 34.34, 52.58, 65.53, 78.78, 88.82, 111.11, 121.86, 126.29, 127.94, 129.94, 130.06, 132.54, 133.05, 135.28, 135.51, 150.35, 150.65, 153.24, 164.04. Analysis for $C_{41}H_{54}O_4N_2Sis$ Calcd.: C, 70.45; H, 7.79; N, 4.01. Found: C, 70.30; H, 7.84; N, 4.03.

EXAMPLE 6

One Vessel Reaction of Compound 2 with Phenylsulfenyl chloride and Silylated thymine One-pot Reaction of Dihydrofuran with Phenylsulfenyl chloride (PhSCl) and Silylated-thymine

| Entry | Lewis Acid[a] | Solvent | Condition[b] | Ratio[c] (11a:11b) | Time (h) | Yield[d] (%) |
|---|---|---|---|---|---|---|
| 1 | SnCl$_4$ | CH$_2$Cl$_2$ | −78 to 0° C. to r.t. | 32:1 | 1.5 | 60 |
| 2 | SnCl$_4$ | Et$_2$O | −78 to 0° C. to r.t. | 6:1 | 1.5 | 45 |
| 3 | TMSOTf | CH$_2$Cl$_2$ | −78 to 0° C. to r.t. | 4:1 | 1.5 | 50 |
| 4 | SnCl$_4$ | CH$_2$Cl$_2$ | −78° C. to r.t. | 42:1 | 2 | 68 |

5'-O-t-Butyldiphenylsilyl-2'α-phenylthio-3'-deoxy-β-thymidine (11) (entry 5 of Table 6)

Compound 2 (0.1808 g, 0.53 mmol, 1.0 eq) was dissolved in 3 mL of dry CH$_2$Cl$_2$ and cooled to −78° C. A freshly prepared sample of phenylsulfenyl chloride (0.0966 g, 0.66 mmol, 1.25 eq) was dissolved in 2 mL of CH$_2$Cl$_2$ and then added to the solution of compound 2. The reaction mixture was stirred under N$_2$ for 30 minutes. After SnCl$_4$ (1.0M in CH$_2$Cl$_2$, 0.61 mL, 0.61 mmol, 1.15 eq) was added, a CH$_2$Cl$_2$ solution (1 mL) of silylated thymine (0.1661 g, 0.61 mmol, 1.15 eq) was added to the reaction mixture. The mixture was stirred for 10–20 min at −78° C. and then allowed to warm to room temperature for about 1 hour. The solution was poured into an aqueous NaHCO$_3$ solution (30 mL) and extracted with 3×25 ml of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography (1:1 of EtOAc/hexanes as eluent) to give 0.2081 g of a white powder in 68% yield, which was an inseparable mixture of 11a and 11b with a ratio of 42:1 determined from $^1$H NMR by integration of the protons at the anomeric center. (d: 6.07d, J=7.5 Hz, b; 6.24-d, J=4.2 Hz, a).

m.p.: 152°–154° C. IR (CH$_2$Cl$_2$, cm$^{-1}$): 3402, 3063, 2940, 1690, 1479, 1270, 1120. $^1$H NMR (300 MHz, CDCl$^3$): d 1.19 (s, 9H), 1.46 (s, 3H), 2.18 (m, 1H), 2.56 (m, 1H), 3.69 (dd, 1H, J=2.4 Hz, J=11.4 Hz), 3.80 (quartet, 1H, J=9.4 Hz), 4.03 (dd, 1H, J=11.4 Hz), 4.25 (m, 1H), 6.07 (d, 1H, J=7.5 Hz) 7.20 (s, 1H), 7.24 (m, 2H), 7.43 (m, 9H), 7.67 (m, 4H), 8.17 (s, 1H). $^{13}$C NMR (75.1 MHz, CDCl$_3$): d 11.85, 19.49, 27.10, 32.53, 49.83, 65.91, 89.14, 111.27, 127.98, 128.01, 128.84, 129.06, 130.04, 130.16, 132.02, 132.39, 133.09, 133.78, 134.88, 135.26, 135.53, 150.50, 163.55.

Analysis for C$_{32}$H$_{36}$O$_4$N$_2$SiS Calcd.: C, 67.10; H, 6.34; N, 4.89. Found: C, 67.12; H, 6.33; N, 5.01.

EXAMPLE 7

One Vessel Reaction of Compound 2 with 2-Nitrophenylsulfenyl chloride and Silylated thymine One-pot Reaction of Dihydrofuran with 2-Nitrophenylsulfenyl chloride (2-O$_2$NPhSCl) and Silylated-thymine

| Entry | Lewis Acid[a] | Solvent | Condition[b] | Ratio[c] (12a:12b) | Time (h) | Yield[d] (%) |
|---|---|---|---|---|---|---|
| 1 | SnCl$_4$ | CH$_2$Cl$_2$ | −78 to 0° C. to r.t. | 20:1 | 13 | 42 |
| 2 | SnCl$_4$ | CH$_2$Cl$_2$ | −78° C. to r.t. | 100:0 | 13 | 55 |

5'-O-t-Butyldiphenylsilyl-2'α-2-nitrophenylthio-3'- deoxy-β- thymidine (12a) (entry 2 of Table 7)

Compound 2 (0.1864 g, 0.55 mmol, 1.0 eq) was dissolved in 3 mL of dry CH$_2$Cl$_2$ and cooled to −78° C. 2-Nitrophenylsulfenyl chloride (0.1201 g, 0.63 mmol, 1.15 eq) was dissolved in 2 mL of CH$_2$Cl$_2$ and then added to the solution of compound 2. The reaction mixture was stirred under N$_2$ for 30 minutes. After SnCl$_4$ (1.0M in CH$_2$Cl$_2$, 0.63 mL, 0.63 mmol, 1.15 eq) was added to the solution, a CH$_2$Cl$_2$ solution (1 mL) of silylated thymine (0.1713 g, 0.63 mmol, 1.15 eq) was added to the reaction mixture. The mixture was stirred for 10–20 minutes at −78° C. and then allowed to warm to room temperature for about 12 hours. The solution was poured into an aqueous NaHCO$_3$ solution (30 mL) and extracted with 3×25 mL of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography to give 0.1427 g of 12a as a yellow powder in 42% yield.

m.p.: 77°–80° C. IR (CH$_2$Cl$_2$, cm$^{-1}$): 3400, 3080, 2980, 2940, 1695, 1530, 1478, 1350. $^1$H NMR (300 MHz, CDCl$_3$): d 1.12 (s, 9H), 1.58 (s, 3H), 2.14 (quin, 1H, J=6.6 Hz), 2.69 (quin, 1H, J=6.6 Hz), 3.75 (dd, 1H, J=2.4 Hz, J=11.4 Hz), 4.09 (m. 2H), 4.40 (m, 1H), 6.07 (d, 1H, J=5.7 Hz), 7.29–7.47 (m, 9H), 7.66 (d, 4H, J=7.2 Hz), 8.06 (d, 1H, J=8.1 Hz), 8.56 (br, s, 1H). $^{13}$C NMR (75.1 MHz, CDCl$_3$): d 12.11, 19.49, 21.10, 32.80, 48.97, 65.11, 79.21, 89.53, 111.59, 125.84, 126.65, 128.00, 128.02, 130.10, 130.18, 130.25, 132.54, 132.73, 133.03,133.15, 135.07, 135.34, 135.50, 148.39, 150.42, 163.88.

Analysis for C$_{32}$H$_{35}$O$_6$N$_3$SiS Calcd.: C, 62.21; H, 5.71; N, 6.80 Found: C, 62.57; H, 6.13; N, 6.43.

EXAMPLE 8

One Vessel Reaction of Compound 2 with 4-Nitrophenylsulfenyl chloride and Silylated thymine.

One-pot Reaction of Dihydrofuran with 4-Nitrophenylsulfenyl chloride (4-O$_2$NPhCl) and Silylated-thymine -continued

| Entry | Lewis Acid[a] | Solvent | Condition[b] | Ratio[c] (13a:13b) | Time (h) | Yield[d] (%) |
|---|---|---|---|---|---|---|
| 1 | SnCl$_4$ | CH$_2$Cl$_2$ | –78 to 0° C. to r.t. | 20:1 | 13 | 74 |
| 2 | SnCl$_4$ | CH$_2$Cl$_2$ | –78° C. to r.t. | 25:1 | 13 | 51 |

5'-O-t-Butyldiphenylsilyl-2'α-4-nitrophenylthio-3'-deoxyβ-thymidine (13) (entry 2 of Table 8)

Compound 2 (0.1864 g, 0.55 mmol, 1.0 eq) was dissolved in 3 mL of dry CH$_2$Cl$_2$ and cooled to –78° C. 4-Nitrophenylsulfenyl chloride (0.1201 g, 0.63 mmol, 1.15 eq) was dissolved in 2 mL of CH$_2$Cl$_2$ and then added to the solution of compound 2. The reaction mixture was stirred under N$_2$ for 30 minutes. After SnCl$_4$ (1.0M in CH$_2$Cl$_2$, 0.63 mL, 0.63 mmol, 1.15 eq) was added to the solution, a CH$_2$Cl$_2$ solution (1 mL) of silylated thymine (0.1713 g, 0.63 mmol, 1.15 eq) was added to the reaction mixture. The mixture was stirred for 10–20 minutes at –78° C. and then allowed to warm to room temperature for about 12 hours. The solution was poured into an aqueous NaHCO$_3$ solution (30 mL) and extracted with 3×25 ml of CH$_2$Cl$_2$. The combined CH$_2$Cl$_2$ layer was washed with 50 mL of brine solution before being dried with anhydrous MgSO$_4$. After filtration and concentration, the resulting crude product was purified by flash silica gel chromatography to give 0.1723 g of a yellow powder in 51% yield, which was an inseparable mixture of 13a and 13b with a ratio of 25:1 determined from $^1$H NMR by integration of the protons at the anomeric center. ( d: 6.07-d, J=6.0 mL, b; 6.35-d, J=6.0 Hz, a ). m.p.: 76°–79° C. IR (CH$_2$Cl$_2$, cm$^{-1}$): 3400, 3070, 2950, 2880, 1700, 1525, 1480, 1345. $^1$H NMR (300 MHz, CDCl$_3$): d 1.10 (s, 9H), 1.58 (s, 3H), 2.15 (quin, 1H, J=6.5 Hz), 2.64 (quin, 1H, J=6.5 Hz), 3.77 (dd, 1H, J=2.4 Hz, J=11.4 Hz), 4.02 (quartet, 1H, J=6.2 Hz), 4.14 (m, 1H), 4.38 (m, 1H), 6.07 (d, 1H, J=6.0 Hz), 7.25–7.49 (m, 10H), 7.67(d, 4H, J=7.2 Hz), 8.07 (d, 1H, J=8.7 Hz). $^{13}$C NMR (75.1 MHz, CDCl$_3$): d 12.09, 19.50, 27.10, 32.82, 49.67, 65.23, 79.16, 89.10, 111.71, 123.95, 127.87. 128.03, 128.05, 130.17, 130.24, 130.39, 132.43, 132.92, 134.60, 135.30, 135.48, 135.54, 135.57, 143.06, 146.40, 150.58, 163.86.

Analysis for C$_{32}$H$_{35}$O$_6$N$_3$SiS Calcd: C, 62.21; H, 5.71; N, 6.80. Found: C, 62.26; H, 5.93; N, 6.48.

EXAMPLE 9

One Vessel Reaction of Compound 2 with 2,4,6-Triisopropylphenylsulfenyl chloride (TIPPSCl) and Silylated-Uracil One-pot Reaction of Dihydrofuran with 2,4,6-Triisopropylphenylsulfenyl chloride (TIPPSCl) and Silylated-Uracil

| Entry | Lewis Acid[a] | Solvent | Condition[b] | Ratio[c] (14a:14b) | Time (h) | Yield[d] (%) |
|---|---|---|---|---|---|---|
| 1 | SnCl$_4$ | CH$_2$Cl$_2$ | −78 to 0° C. to r.t. | 39:1 | 1.5 | 57 |
| 2 | SnCl$_4$ | CH$_2$Cl$_2$ | −78° C. to r.t. | 100:0 | 2 | 52 |

5'-O-t-Butyldiphenylsilyl-2'α-(2,4,6 - triisopropyl) phenylthio-3'-deoxy-β-uridine (14) (entry 1 of Table 9)

Compound 2 (0.2291g, 0.68 mmol, 1.0 eq) was dissolved in 5 mL of dry CH$_2$Cl$_2$ and cooled to −78° C. A freshly prepared sample of 2,4,6-triisopropylphenylsulfenyl chloride (0.2292 g, 0.85 mmol, 1.25 eq) was dissolved in 2 mL of CH$_2$Cl$_2$ and then added to the dihydrofuran solution. The reaction mixture was stirred under N$_2$ for 30 minutes. After SnCl$_4$ (1.0M in CH$_2$Cl$_2$, 0.78 mL, 0.78 mmol, 1.15 eq) was added to the solution, a CH$_2$Cl$_2$ solution (1 mL) of silylated uracil (0.1995 g, 0.78 mmol, 1.15 eq) was added to the reaction mixture. The reaction turned red brown. The mixture was stirred for 10–20 minutes at −78° C. and then allowed to warm to room temperature for about 1 hour. The solution was poured into an aqueous NaHCO$_3$ solution (30 mL) and extracted with 3×25 mL of CH$_2$Cl$_2$. The combined CH$_2$Cl$_2$ layer was washed with 50 ml of brine solution before being dried with anhydrous MgSO$_4$. After filtration and concentration, the resulting crude product was purified by flash silica gel chromatography (1:3 of EtOAc/hexanes as eluent) to give 0.2368 g of 14a as a white foam in 51% yield. m.p.: 73°–76° C.

IR (CH$_2$Cl$_2$, cm$^{-1}$): 3400, 3075, 2980, 2880, 1700, 1470, 1440, 1120. $^1$H NMR (300 MHz, CDCl$_3$): d 1.02 (s, 9H), 1.25 (m, 12H), 1.27 (d, 6H, J=6.6 Hz), 2.05 (m, 1H), 2.44 (quin, 1H, J=7.5 Hz), 2.88 (quin, 1H, J=6.6 Hz), 3.45 (quin, 1H, J=3.9 Hz), 3.71 (dd, 1H, J=2.4 Hz, J=12 Hz), 3.80 (quin, 2H, J=6.6 Hz), 4.11 (dd, 1H, J=2.1 Hz, J=12 Hz), 4.49 (m, 1H), 5.35 (dd, 1H, J=1.8 Hz, J=11.1 Hz, 5.97 (d, 1H, J=3.6 Hz), 7.08 (s, 2H), 7.40 (m, 6H), 7.60 (d, 4H, J=6.6 Hz), 7.76 (d, 1H, J=8.1 Hz), 8.35 (br, s,1H). $^{13}$C NMR (75.1 MHz, CDCl$_3$): d 19.30, 23.94, 24.47, 26.94, 31.70, 32.45, 34.31, 53.90, 64.66, 80.52, 89.68, 102.06, 122.00, 125.83, 127.95, 130.05, 130.10, 132.37, 132.81, 135.37, 135.56, 139.98, 150.12, 150.44, 153.40, 163.55. Analysis for C$_{40}$H$_{52}$O$_4$N$_2$SiS Calcd.: C, 70.14; H, 7.65. Found: C, 70.08; H, 7.89.

V. Condensation of 5-(S)-(protected-oxy) -2,3-dihydrofuran with Purine Bases

A. Preparation of Compound 15: Reaction of Compound 2 with 2,4,6-Triisopropylphenylsulfenyl chloride and Silylated 6-chloropurine To 0.480 mmol of 2,4,6-triisopropylphenylsulfenyl chloride dissolved in 3.1 mL of diethyl ether at −78° C. was added 150 mg (0.443 mmol) of compound 2 dissolved in 1.3 mL of ether, down the side of the flask over a 10 minute period. This mixture was stirred at −78° C. for 30 minutes prior to the sequential addition of a solution of 120 mg (0.529 mmol) of silylated 6-chloropurine in 2.2 mL of ether, and 0.12 mL (0.600 mmol) TMSOTf. After stirring an additional 10 minutes at −78° C., the reaction mixture was removed from the −78° C. bath, allowed to warm to room temperature and subsequently stirred for 2 hours. The reaction was then quenched by dilution to 50% with ether followed by exposure to a saturated solution of NaHCO$_3$. The organic layer was separated and washed with brine. Following the re-extraction of the aqueous layers with ether the combined organic layers were dried over anhydrous MgSO$_4$. Filtration followed by solvent removal in vacuo yielded only one isomer as determined by NMR spectroscopy. Column chromatography (9:1 hexane:ethyl acetate) yielded 96.7 mg (0.131 mmol), 31% of pure material that was determined to be the N$^9$ β isomer (15) by high field NMR experiments (COSY, and 1-dimensional NOE). Physical Data for 15: $^1$H NMR: 1.027 ppm (s, 9 H); 1.124 ppm (dd, 12 H); 1.223 ppm (d, 6H); 2.101 ppm (m, 1H); 2.576 ppm (m, 1H); 2.832 ppm (quint, 1 H) ; 3.742 ppm (m, and dd, 3 H); 3.976 ppm (dd, 1 H); 4.062 ppm (m, 1 H); 4.632 ppm (m, 1 H) ; 6.026 ppm (d, 1 H); 6.940 ppm (s, 2H); 7.345 ppm (m, 6 H); 7.594 ppm (dd, 4 H); 8.178 ppm (s, 1 H); 8.511 ppm (s, 1 H).

(ii) In Toluene:

Following the previous procedure, 0.480 mmol 2,4,6-triisopropylphenylsulfenyl chloride, 150 mg (0.443 mmol), compound 2, 120 mg (0,529 mmol) of silylated 6-chloropurine, and 0.12 mL (0,600 mmol) TMSOTf in toluene gave mixtures of what appear to be the αN$^9$ and βN$^9$ isomers (by proton NMR determination).

(iii) In Acetonitrile: Following the previous procedure, 0.480 mmol 2,4,6-triisopropylphenylsulfenyl chloride, 150 mg (0.443 mmol) compound 2, 120 mg (0.529 mmol) of silylated 6-chloropurine, and 0.12 mL (0.600 mmol) TMSOTf in acetonitrile (as described in the previous procedure) gave mixtures of what we presume to be the αN$^9$ and β-N$^9$ isomers (by proton NMR determination).

(iv) In Methylene Chloride: Following the previous procedure, 0.480 mmol 2,4,6-triisopropylphenylsulfenyl chloride, 150 mg (0.443 mmol), compound 2, 120 mg (0.529 mmol) of silylated 6-chloropurine, and 0.12 mL (0.600 mmol) TMSOTf in methylene chloride (as described in the previous procedure) unfortunately only yielded polymerized starting material.

B. Compound 16: Reaction of Compound (2) with 2, 4, 6-triisopropylphenylsulfenyl chloride and Silylated $N^6$-benzoyl Adenine.

To 0.554 mmol of 2,4,6-triisopropylphenylsulfenyl chloride dissolved in 3.1 mL of methylene chloride ($CH_2Cl_2$) at −78° C. was added 150 mg (0.443 mmol) of the dihydrofuran (2) dissolved in 1.3 mL of $CH_2Cl_2$, down the side of the flask over a 10 minute period. This mixture was stirred at −78° C. for 30 minutes prior to the sequential addition of a solution of 200 mg (0.519 mmol) of bis-silylated $N^6$-benzoyl adenine in 2.2 mL of ether, and 0.12 mL (0,600 mmol) TMSOTf. After stirring an additional 10 minutes at −78° C., the reaction mixture was removed from the −78° C. bath, allowed to warm to room temperature and subsequently stirred for 2 hours. The reaction was then quenched by dilution to 50% with $CH_2Cl_2$ followed by exposure to a saturated solution of $NaHCO_3$. The organic layer was separated and washed with brine. Following the re-extraction of the aqueous layers with $CH_2Cl_2$, the combined organic layers were dried over anhydrous $MgSO_4$. Filtration followed by solvent removal in vacuo yielded predominantly one isomer. Spectroscopic details, although obtained in crude fashion, will be withheld until further purification is accomplished.

C. Compound 17: Reaction of Compound (2) with 2, 4, 6-triisopropyl-phenysulfenyl chloride and Silylated Hypoxanthine.

To 0.554 mmol of 2,4,6-triisopropylphenylsulfenyl chloride dissolved in 3.1 mL of diethyl ether (ether from this point on) at −78° C. was added 150 mg (0.443 mmol) of the dihydrofuran (2) dissolved in 1.3mL of ether, down the side of the flask over a 10 minute period. This mixture was stirred at −78° C. for 30 minutes prior to the sequential addition of a solution of 200 mg (0.531 mmol) of bis-silylated hypoxanthine in 2.2 mL of ether, and 0.12 mL (0.600 mmol) TMSOTf. After stirring an additional 10 minutes at −78° C., the reaction mixture was removed from the −78° C. bath, allowed to warm to room temperature and subsequently stirred for 2 hours. The reaction was then quenched by dilution to 50% with ether followed by exposure to a saturated solution of $NaHCO_3$. The organic layer was separated and washed with brine. Following the re-extraction of the aqueous layers with ether, the combined organic layers were dried over anhydrous $MgSO_4$. Filtration followed by solvent removal in vacuo yielded predominantly one isomer. Spectroscopic details, although obtained in crude fashion, will be withheld until further purification is accomplished.

This invention has been described with reference to its preferred embodiments. Variations and modifications of the invention will be obvious to those skilled in the art from the foregoing detailed description of the invention. It is intended that all of these variations and modifications be included within the scope of the appended claims.

We claim:

1. A process for the preparation of a compound selected from the group consisting of 2',3'-didehydronucleosides, 2'-deoxynucleosides, and 2',3'-dideoxy-2',3'-didehydronucleosides comprising:

A) forming a 5'-(protected oxy)-2'α-(arylsulfenyl)-3'(Q)-β-purine or pyrimidine nucleoside by reacting in one vessel i) a 5-(S)-6-(protected oxy)-4-Q-4,5-dihydrofuran of the structure wherein Q is selected from the group consisting of hydrogen, $N_3$, OH, halo, alkyl, aryl, $NH_2$, and O-alkyl;

(ii) a protected purine or pyrimidine base;

(iii) a Lewis acid which catalyzes the glycosylation of the base with the dihydrofuran with high β-stereoselectivity; and (iv) an aryl sulfenyl compound of the structure wherein Z is any appropriate leaving group under the conditions of reaction, X is alkyl, aryl, nitro, halo, or CN, and n is 0, 1, 2, 3, 4, or 5; and then B) removing the 2-α-sulfenyl moiety.

2. The process of claim 1, wherein the leaving group is selected from the group consisting of halo, -O-C(O) (alkyl or aryl), -NH-C(O) (alkyl or aryl), and —$SO_2$(alkyl or aryl).

3. The process of claim 1 wherein the product is a 2',3'-didehydro-2',3'- dideoxynucleoside, further comprising treating the 5'-protected(oxy)-2'-α-(arylsulfenyl)-3'-(Q)-β-purine or pyrimidine nucleoside with a peroxy acid followed by heat.

4. The process of claim 1, wherein the product is a 2',3'-dideoxynucleoside, further comprising treating the 5'-protected(oxy)-2'-α-(arylsulfenyl)3'-(O)-β-purine or pyrimidine nucleoside with trialkyl tin hydride.

5. The process of claim 1, wherein Q is selected from the group consisting of H and OH.

6. The process of claim 1, wherein Q is $N_3$.

7. The process of claim 1 wherein the oxygen protecting group is selected from the group of consisting of trisubstituted silyl, trityl, alkyl, acyl, methyl sulfonyl, and p-toluenesulfonyl.

8. The process of claim 1 wherein the base is a pyrimidine.

9. The process of claim 8 wherein the Lewis acid is $SnCl_4$.

10. The process of claim 1 wherein the base is purine.

11. The process of claim 10 wherein the Lewis acid is TMSOTf.

* * * * *